United States Patent [19]

Hartman et al.

[11] Patent Number: 5,065,614
[45] Date of Patent: Nov. 19, 1991

[54] SHORT PATH THERMAL DESORPTION APPARATUS FOR USE IN GAS CHROMATOGRAPHY TECHNIQUES

[75] Inventors: Thomas G. Hartman, Staten Island, N.Y.; John J. Manura, Pennington, N.J.; Santford V. Overton, Ringoes, N.J.; Christopher W. Baker, Lambertville, N.J.; John N. Manos, Trenton, N.J.

[73] Assignee: Rutgers University, New Brunswick, N.J.

[21] Appl. No.: 560,440

[22] Filed: Jul. 31, 1990

[51] Int. Cl.$^5$ .............................................. G01N 30/18
[52] U.S. Cl. .................................. 73/23.35; 73/23.41
[58] Field of Search ................ 73/23.35, 23.37, 23.41, 73/23.42, 23.25

[56] References Cited

U.S. PATENT DOCUMENTS 3,374,660  3/1968  McKinney et al. ............ 73/23.35 X
4,089,207  5/1978  Patton ................................ 73/23.35

Primary Examiner—Hezron E. Williams
Assistant Examiner—Joseph W. Roskos
Attorney, Agent, or Firm—Lerner, David, Littenberg, Krumholz & Mentlik

[57] ABSTRACT

A short path thermal desorption apparatus for use in a gas chromatoagraphy-detector unit (GC-DET) such as a gas chromatography-mass spectrometry system has a housing defining an upper compartment, and a desorption compartment. An upper front panel on the housing has an elongated longitudinally disposed opening which provides communication between the upper compartment and the exterior of the housing. An injection assembly is disposed at the exterior of the housing adjacent the upper front panel and is actuated from a disengaged position to an engaged position with the gas chromatography unit by a suitable gas powered cylinder mounted in the upper compartment. The injection assembly includes, a desorption tube for collecting and storing the sample compound to be analyzed and includes, means for passing a carrier gas therethrough to desorb the sample component when the desorption unit is heated, and a needle injector for passing the desorbed sample component to the GC-DET system for identification and quantification of the sample component. The desorption tube is operatively associated with a desorption block assembly having a pair of coacting heating blocks made of materials having a high coefficient of heat transfer and mounted for bilateral opening and closing about the desorption tube when the injection assembly is moved from the disengaged to the engaged position.

4 Claims, 6 Drawing Sheets

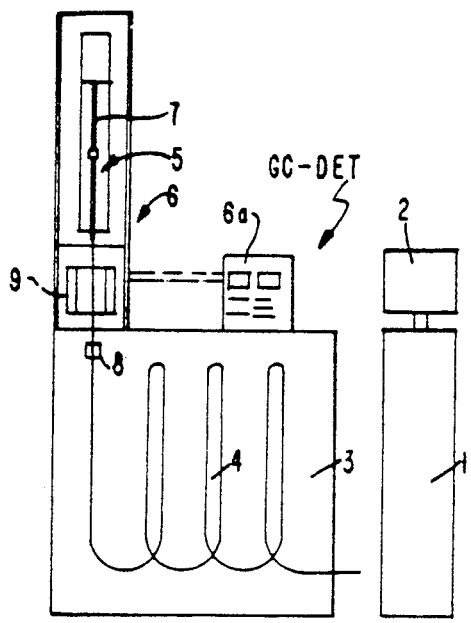
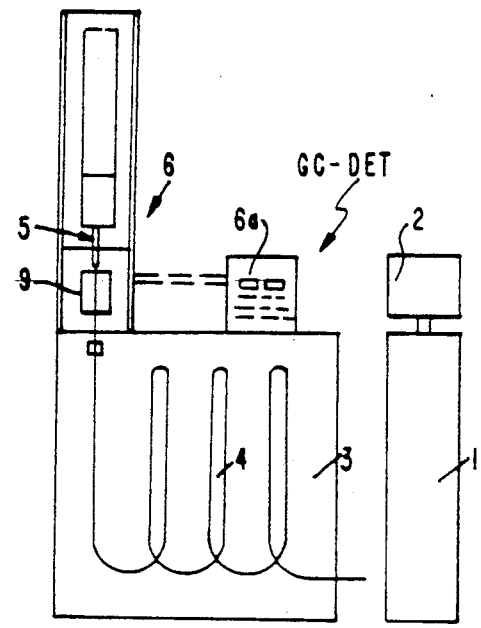
FIG. 1A
FIG. 1B
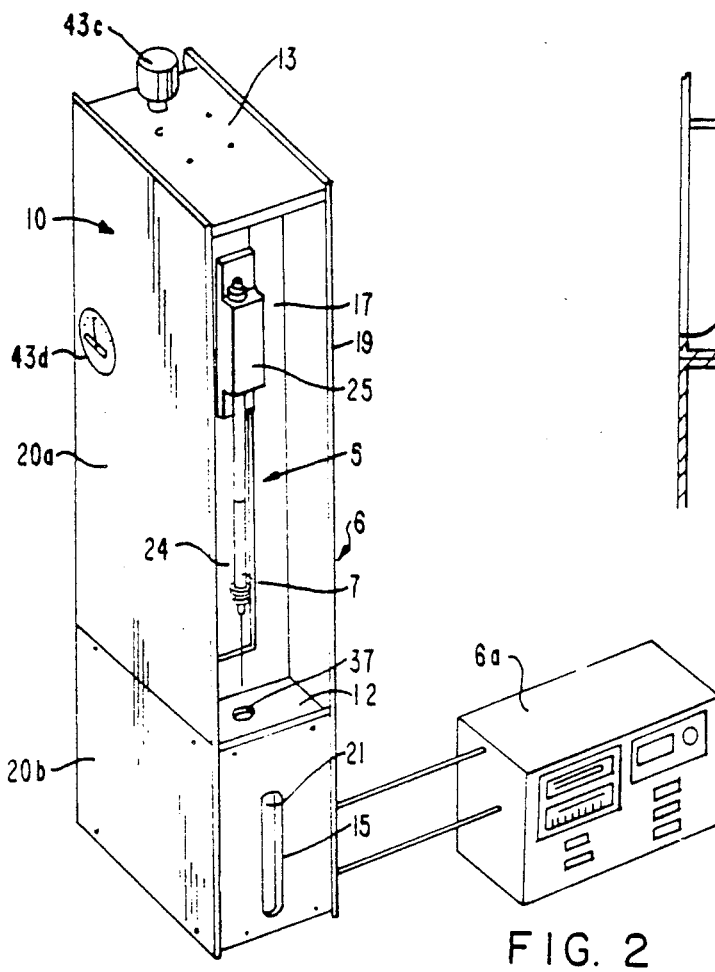
FIG. 2
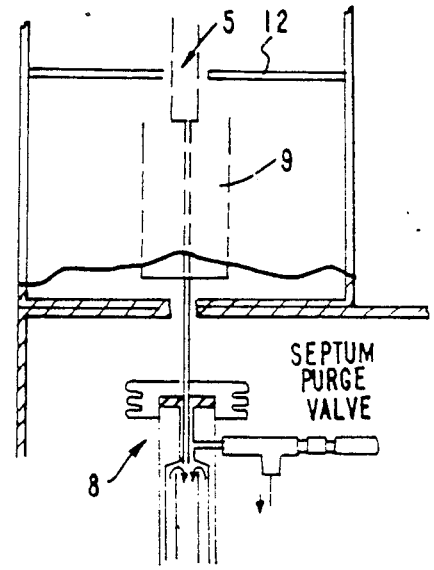
FIG. 1C

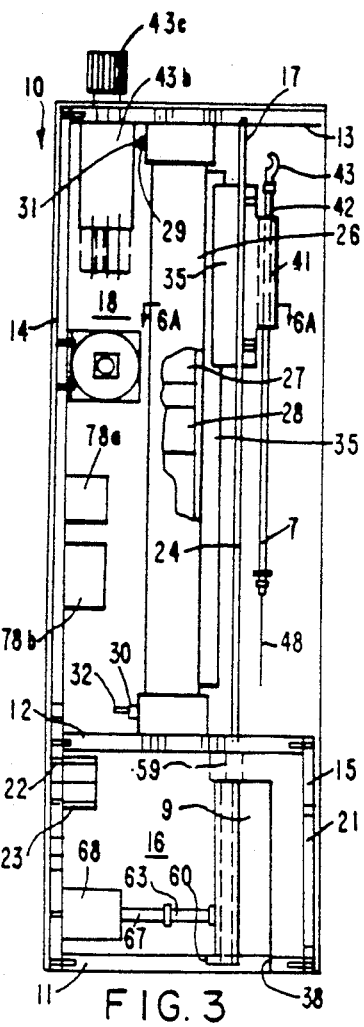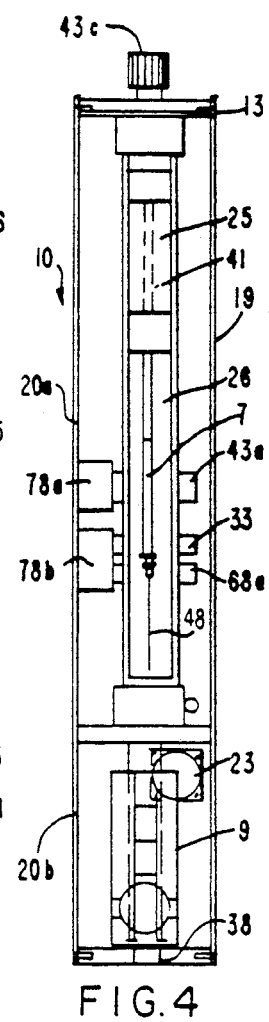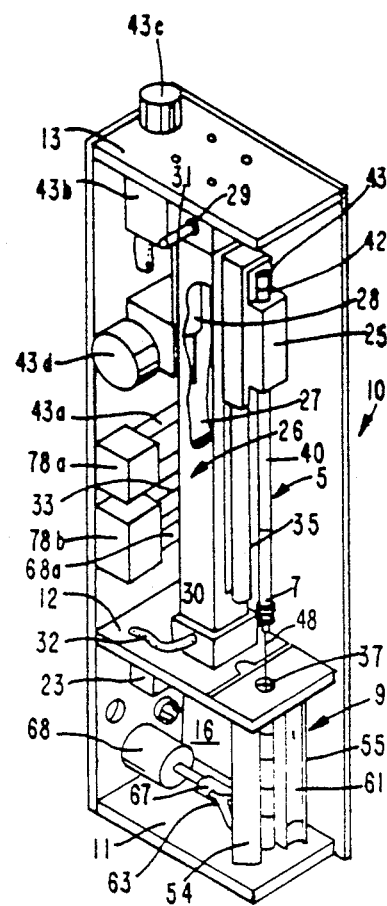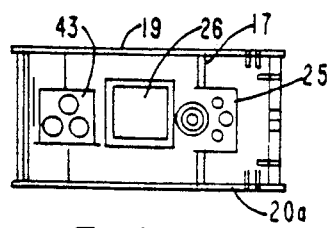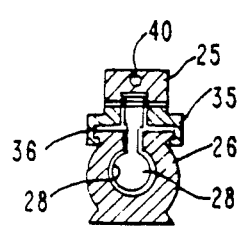

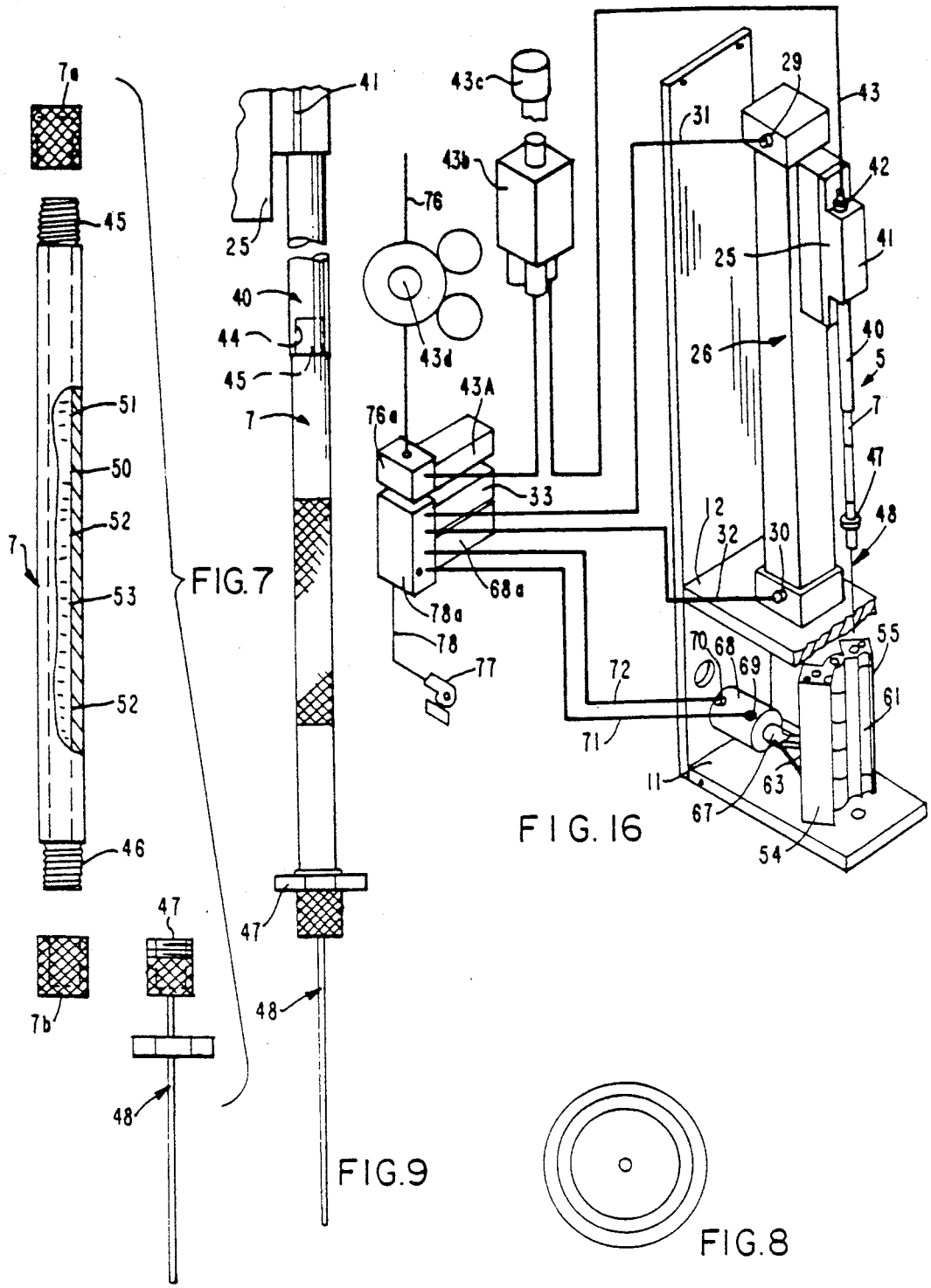

LOAD POSITION

INJECTION COMPLETE

HEAT AND DESORB

SHORT PATH THERMAL DESORPTION APPARATUS FOR USE IN GAS CHROMATOGRAPHY TECHNIQUES

This invention relates particularly to a short path thermal desorption apparatus for use in any of the several gas chromatography techniques which include a variety of detectors such as mass spectrometry (GC-MS), fourier transform infrared spectrometry (GC-FTIS), flame ionization detection (FID), electron capture detection (GC-ECD), thermal conductivity detection (GC-TCD), flame photometric detection (GC-FPD), and hall electron conductivity detection (GC-HCD) for the identification and quantitative determination of both volatile and semi-volatile components in complex materials such as foods, beverages, cosmetics and pharmaceuticals, in the forensic sciences, such as arson investigations and in environmental industrial hygiene including, drug analysis and sewage analysis and other complex materials.

BACKGROUND OF THE INVENTION

Thermal Desorption Units and On-Column Injection Capillary and Packed Columns for Gas Chromatography Units have been successfully utilized in a variety of systems, methods and techniques for the separating, analyzing, identifying and recording both volatile and semi-volatile components in complex materials.

Capillary and packed columns for Gas Chromatography Units used in such systems, methods and techniques are generally classified by bore size. Thus, micro-bore capillary columns will have internal diameters, (I.D.'s), in the order of 0.25 mm or 0.32 mm; and macro-bore or mega-bore capillary columns will have an I.D. in the order of 0.53 mm or 0.75 mm. Packed Columns for Gas Chromatography Units have much larger I.D.'s in the order of 2.0 mm to 4.6 mm. The respective internal diameters (I.D.'s) will affect the quantities and rates at which carrier gas with the volatile or semi-volatile component to be identified and quantified is passed to the Gas Chromatography Unit.

Purge and trap thermal desorption gas chromatography-mass spectrometry is particularly suited to the isolation and identification of volatile components such as flavors in foods and beverages and other volatile and semi-volatile components in other complex matrices. The general method for use with this equipment requires at least the following steps:

1. Separation and Storage of the Component

Volatile components are sparged from numerous complex matrices such as gases, water, foods, beverages, cosmetics, petrochemicals and pharmaceuticals. These volatile components are passed into a sized collecting container having a predetermined trapping agent such as the porous polymer resin, 2, 6-diphenyl-p-phenyleneoxide sold under the trademark TENAX-TA or the activated graphitized carbon sold under the trademark CARBOTRAP for collecting and adsorbing thereon the particular volatile or semi-volatile component being determined. Both of the above enumerated trapping agents have a high affinity for non-polar organic compounds and a very low affinity for water vapor and other low molecular weight polar compounds such as alcohols with less than three carbon atoms.

While these trapping agents have been referred to and described, those skilled in the art will recognize that there are many other adsorbent materials which can function equally as well and that these trapping agents where referred to in the present Application are only by way of illustration and not intended to limit use of such other adsorbent materials as may also be used within the scope of the present invention.

With these trapping agents, when the sparged marked volatile or semi-volatile components are passed into the collecting container the water vapor will pass through the trapping agent and the volatile component will be adsorbed onto the surface of the trapping agent. Once the component is separated and trapped the sample is stored by sealing the sized collecting chamber until it is ready to be identified and quantified in any appropriate one of the enumerated gas chromatography-detector systems, methods or techniques.

2. Release and Delivery of the Component

The sized collecting container is placed in suitable apparatus where it can be heated to thermally desorb the volatile or semi-volatile components.

Then the desorbed volatile or semi-volatile component is passed or delivered by any suitable means to the gas chromatography unit where the volatile component and the marker compound are separated.

3. Monitoring Identification and Quantifying

By the operative coaction of the detector and its monitoring equipment with the gas chromatography unit, the separated volatile components are continuously monitored, and analyzed, and the results are recorded on and can be read out from the monitoring equipment. One such detector for this purpose is a mass spectrometer and reference will be made herein to such gas chromatography-mass spectrometer (GC-MS) by way of illustration only. However, those skilled in the art will recognize that the combination of the short path thermal desorption apparatus in accordance with the present invention with the gas chromatography unit is adapted for universal use in any of the gas chromatography-detector systems, methods and techniques, as was above enumerated, without departing from the scope and use of the present invention.

In older and currently known prior art desorption type purge and trap methodology a unitary device is used which includes, a purge and trap chamber, thermal desorption means for the marker compound and other volatile components of the complex matrix material being analyzed, transfer lines, and cryotraps. In these systems the adsorbent trap is an integral part of the apparatus and cannot be easily removed or replaced. It therefore is necessary to backflush the apparatus to clear it for the next sample to eliminate contamination and other side affects which will affect the nature and tend to degrade the component being analyzed.

In purge and trap methodology in which the desorption tube is desorbed in a heating chamber, the carrier gas will in addition to volatile component pickup artifacts which may be on the outside of the desorption tube, thus affecting the integrity of the sample component and the accuracy of the identification and quantification of the sample component.

These prior art systems do not work well for higher boiling point components or for general purpose volatile components, because they produce cross contamination between the samples being tested, have a memory effect between samples due to sample overload and repetitive analysis of many samples. Additionally, the transfer lines to the inlet port of the gas column of the gas chromatography unit are relatively long and this causes a measurable loss of resolution and produces some catalytic reaction which degrades labile component samples being analyzed.

The present invention overcomes these prior art problems by providing an improved short path thermal desorption apparatus for use in Gas Chromatography-Detector Techniques such as Gas Chromatography-Mass Spectrometry Systems and Techniques to provide a relative quick and accurate mechanism for achieving in each sample tested the desired qualitative and quantitative determination of either conventional components such as menthol in complex matrices such as food, or more complex components such as fatty acids, high boiling point lipid peroxidation species, less volatile pyrazines, terpenes, sesamol from sesame, thiols, dithiols, disulfides, trisulfides, thoiesters, pheromones, pesticides, and other high boiling point impurities in such complex materials or matrices.

Such short path thermal desorption apparatus in accordance with the present invention provides at least several primary advantages. First, it enables the sample component in a glass lined or fused silica lined stainless steel tube type adsorbent trap to be subjected to ballistic type heating. Second, the desorbed component can be transferred easily and efficiently into the injection port for the gas column for the gas chromatography unit through transfer lines consisting of the short stainless steel type adsorbent trap and its associated needle injection assembly wherein the walls are either coated with a boro-silicate or are fused silica lined, thereby providing in the short transfer path for the sample component an inert environment which minimizes degradation of labile sample components which often decompose upon contact with hot catalytic metal wall surfaces of the transfer path. And third, each sample component has its own individual and new stainless steel tube adsorbent trap and associated needle injection assembly, having an inlet and outlet for the independent charging of fresh carrier gas therethrough to eliminate the possibility of cross-contamination from sample component to sample component, thus preventing any "memory effect" which has heretofore occurred in the prior art desorbing apparatus due to overloading of the adsorbent in the stainless steel type adsorbent trap, as will now be more fully described.

Ballistic Heating when used herein means heating with a sharp rise in the temperature of the desorption tube, at an approximate rate or ramp speed of about 100° C. per minute, to enable the desorption tube to be brought rapidly to the boiling temperature of the volatile or semi-volatile component to be desorbed from the desorption tube.

SUMMARY AND OBJECTS OF THE INVENTION

Thus, the present invention covers a short path thermal desorption apparatus for use in any type of gas chromatography unit-detector systems, methods and techniques comprising, a housing means, an injection assembly disposed at the exterior of the housing, actuating means fixedly connected in said housing and operatively connected to the injection assembly to move the injection assembly from a disengaged position to an engaged position for delivering the component to be measured to the gas chromatography unit, said injection assembly including, an inlet means connected to a controlled source of carrier gas when the injection assembly is moved to the engaged position, a detachably connectible desorption tube for collecting and storing the component to be measured and to be desorbed into the carrier gas flowing through the injection assembly, and a needle injector connected to the desorption tube for receiving the desorbed component and for injecting the same into the gas chromatography unit, and heating means in the housing normally open and movable to a closed position when the injection assembly is moved to the engaged position for operative and controlled heating of the desorption tube to desorb the component to be determined from the desorption tube.

Accordingly, it is object of the present invention to provide a short path thermal desorption apparatus for use in all types of Gas Chromatography-Detector Systems and Methods such as Gas Chromatography-Mass Spectrometry (GC-MS) Systems; GC-IR; GC with flame sulfur electron capture systems, etc. which allows for the qualitative and quantitative determination of both volatile and semi-volatile components in complex materials or matrices.

It is another object of the present invention to provide a short path thermal desorption apparatus which is compact in size, easily transportable, and can be quickly disconnected from one gas chromatography unit, and transferred and reinstalled for use with another gas chromatography unit.

It is another object of the present invention to provide a short path thermal desorption assembly which avoids tedious sample clean-up such as solvent extractions, and subsequent concentrations.

It is another object of the present invention to provide a short path thermal desorption apparatus wherein the volatile or semi-volatile component to be identified and quantified is desorbed from the original collection tube or container and passed to the inlet end of the gas column for the gas chromatography unit over a relatively short path to obtain maximum sensitivity, and both minimum loss or degradation of the sample of such component.

It is another object of the present invention to provide a short path thermal desorption apparatus which permits ballistic heating of the tube or container in which the sample of the volatile or semi-volatile component is stored, to desorb the same easily and accurately at temperatures of up to 300° C. for time periods in a range from thirty (30) seconds to one (1) hour.

It is another object of the present invention to provide a short path thermal desorption apparatus which permits ballistic heating of the tube or container in which the samples of the volatile or semi-volatile component is collected and stored, at ramp rates of 100° C. per minute and attained temperatures of the collecting tube or container, to within $+/-5°$ C.

It is another object of the present invention to provide a short path thermal desorption assembly in which the entire transfer path for the volatile or semi-volatile component sample and the heating zone for desorbing the component sample is either glass lined or fused silica lined to minimize component sample reactions or degradation on the inner surfaces or walls of the transfer path or the desorption tube.

It is another object of the present invention to provide a short path thermal desorption apparatus in which each sample component uses its own desorbent tube and injection needle to prevent "memory effect" due to sample adsorbent tube overloading and cross contamination between samples.

It is still another object of the present invention to provide a short path thermal desorption apparatus which has a separate and fresh quantity of carrier gas for each new desorption tube inserted into the injection assembly, and the entire carrier gas flow is directed through the desorption tube and cannot pick-up any extraneous contaminants from sources on the outer surface or exterior to the desorption tube.

It is still another object of the present invention to provide a desorption block assembly having coacting bilaterally pivoted heating blocks moveable from open to closed position and vice versa, machined from solid blocks of materials with high coefficients of heat transfer which are durable and can be accurately positioned and temperature controlled for optimum heat transfer to the operatively associated desorption tube holding the component sample to be analyzed, and It is another and further object of the present invention to provide a desorption block assembly having a pair of coacting precision machined pivotally mounted heat blocks which can be actuated easily by air operated, hydraulically operated or electrically operated solenoid actuating means.

These and other objects of the invention will be more clearly understood from the following description when read in conjunction with the accompanying drawings, in which:

BRIEF DESCRIPTION OF THE DRAWINGS

FIG. 1A is a schematic diagram of a Column type Gas Chromatography-Mass Spectrometry System including, an improved short path thermal desorption apparatus in accordance with the present invention having the injection assembly in the disengaged position, FIG. 1B is the same schematic diagram shown in FIG. 1A with the injection assembly of the short path thermal desorption apparatus in the engaged position, FIG. 1C is an enlarged fragmentary front view of the lower end of the short path thermal desorption apparatus and the gas chromatography unit as shown in FIGS. 1A and 1B broken away and in cross-section to show the injection assembly in assembled position for engagement with the inlet septum end of the gas column of the gas chromatography unit, FIG. 2 is a perspective view of one preferred form of short path thermal desorption apparatus in accordance with the present invention and its associated electronic controller or data processor unit, FIG. 3 is a left side view of the short path thermal desorption apparatus shown in FIG. 2 with the left side panels of the housing removed, FIG. 4 is a front view of the short path thermal desorption apparatus shown in FIGS. 2, and 3, FIG. 5 is a top plan view of the short path thermal desorption apparatus shown in FIGS. 2, 3 and 4 with the top cover of the housing removed to show respectively, top views of the pressure regulator, the actuator, and the mounting carriage, FIG. 6 is a front perspective view of the short path thermal desorption apparatus as shown in FIG. 2 with various panels of the housing removed to show inter alia, the actuator, the injection assembly, the desorption block assembly operatively associated therewith in open position, and other elements, FIG. 6A is a cross-section taken on line 6A—6A of FIG. 3.

FIG. 7 is an enlarged front view of one form of desorption tube partly broken away to show the fused glass lining, the trapping agent, and the operatively associated end caps, and the injection assembly unit to be connected thereon.

FIG. 8 is a top plan view of the desorption tube shown in FIG. 7,

FIG. 9 is a foreshortened front view showing the means for connecting the desorption tube into the associated elements of the injection assembly, FIG. 16 is a diagrammatic sketch of the pneumatic system and the operatively associated solenoid valves that control the flow of operating gas and carrier gas.

DESCRIPTION OF A PREFERRED EMBODIMENT

Figure 10:
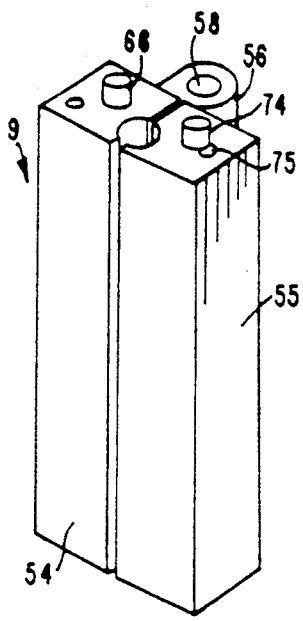
FIG. 10 is a front perspective view of one form of desorption block in the closed position.
Figure 11:
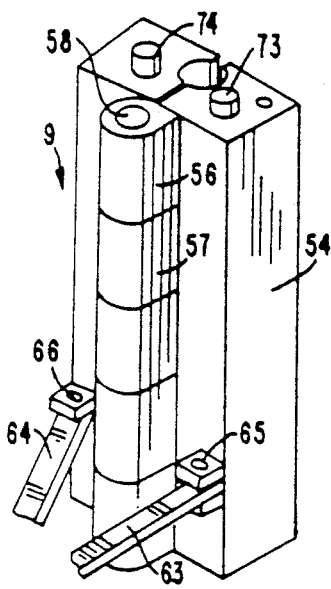
FIG. 11 is a back perspective view of the form of the desorption block as shown in FIG. 10.
Figure 12:
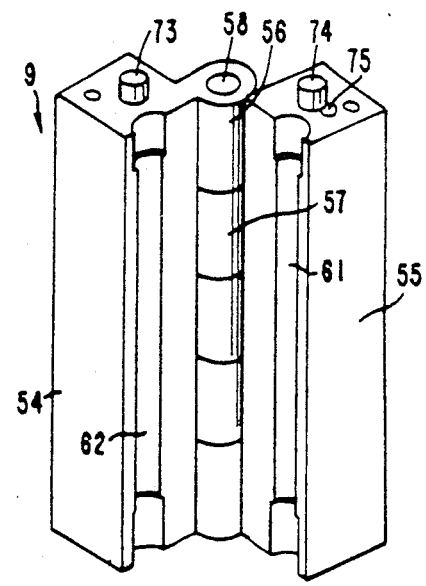
FIG. 12 is a front perspective view of the desorption block shown in FIGS. 10 and 11 in the open position.
Figure 13:
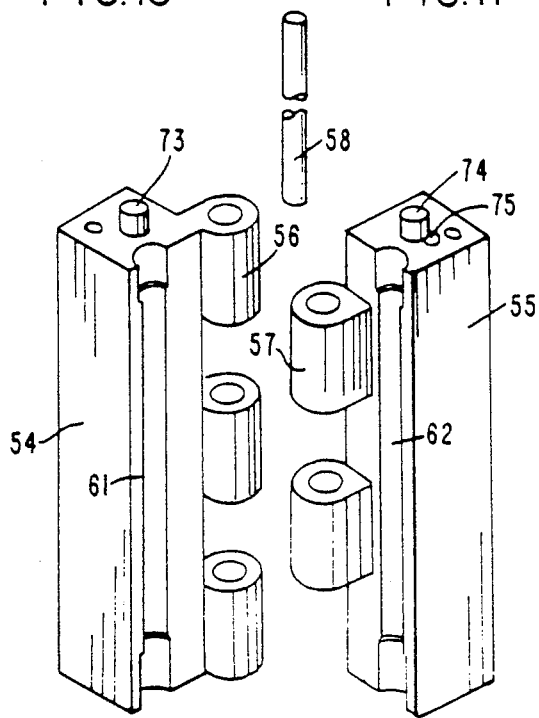
FIG. 13 is an exploded view of the desorption block shown in FIGS. 10, 11 and 12, showing the coacting heating blocks.
Figure 14:
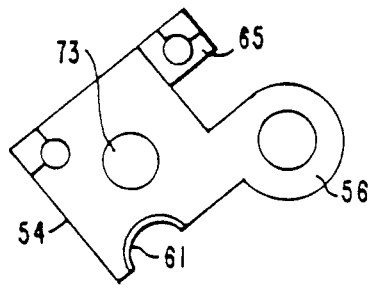
FIG. 14 is a top plan view of the left heating block.
Figure 15:
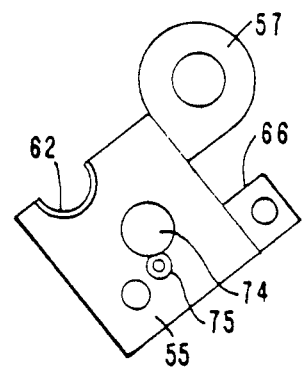
FIG. 15 is a top plan view of the right heating block.

Referring to the drawings FIGS. 1A, 1B and 1C show schematically one form of simple capillary column type Gas Chromatography-Mass Spectrometry System generally designated GC-MS for identifying and quantifying volatile or semi-volatile components of complex materials or matrices such as foods, beverages, cosmetics, and pharmaceuticals.

The present invention is shown as used with a Gas Chromatography-Mass Spectrometry System solely for purpose of illustration. Those skilled in the art will readily understand that the short path thermal desorption apparatus can be universally used in all types of Gas Chromatography-Detector (GC-DET) Systems, Methods and Techniques, and that such usage is intended to come within the scope of the present invention.

The GC-MS System includes, a mass spectrometer 1 having a suitable recording and read-out device such as a recorder, computer or data system 2, a gas chromatography unit 3 with a capillary gas column 4 for fractionating the volatile components as a function of their boiling points so they can be read by the mass spectrometer, and an injection assembly 5 in a short path thermal desorption apparatus 6 in accordance with the present invention having, a removable and replaceable desorption tube or container 7 with the sample component to be identified and quantified adsorbed on a suitable media therein.

The injection assembly is positioned and movable from the disengaged position, as shown in FIG. 1A, to a position where the desorption tube is engaged with a suitable desorption block assembly 9 for heating and desorbing the sample component and for injecting the sample component into the injection port end 8 of the capillary gas column 4 of the gas chromatography unit, as is shown in FIGS. 1B and 1C. Short path thermal desorption apparatus 6 is connected to a suitable electronic controller 6a for providing the desired movement of the injection assembly 5 and the desorption tube 7 and the required operative association with the desorption block assembly 9 for desorbing the sample component and for the injecting of the sample component into the inlet port end 8 of the capillary gas column 4 of the gas chromatography unit 3.

The use of gas chromatography-mass spectrometry and other gas chromatography-detector unit systems, methods and techniques for identifying and quantifying volatile components of complex matrices are available and known in most laboratories. Therefore, it is not necessary to describe either the gas chromatography unit or the mass spectrometer unit in great detail because the structure and operation of these devices and their operative interrelation for this purpose will be readily understood by those skilled in the art.

In the present invention an improved short path thermal desorption apparatus 6 is shown and disclosed for transferring the volatile component to be identified and quantified, a relatively short distance, approximately 4 cm, and injecting the same into the inlet port end 8 of the capillary column 4 of the gas chromatography unit 3. This short path thermal desorption apparatus in accordance with the present invention utilizes a simple form of desorption tube or container hereinafter more fully described having an adsorption media therein and into which the sample volatile component is initially charged and trapped so that when the short path thermal desorption apparatus 6 is in assembled position for operative coaction with the gas chromatography unit 3 the sample volatile component can be desorbed by controlled heating of the desorption tube or container and efficient transfer and injection thereof into the inlet port end 8 of the capillary gas column 4 of the GC-MS System.

The short path thermal desorption apparatus 6 and its electronic controller 6a are compact and portable. Therefore they can be easily disconnected, transferred and reconnected and installed for coaction with any form of gas chromatography unit having a capillary gas column.

Now, referring to FIGS. 2 to 9, and 16, 17A, 17B and 17C of the drawings the short path thermal desorption apparatus is shown as having a generally elongated vertically disposed housing 10 having, a base 11, and intermediate transverse partition 12 a predetermined spaced distance from the base 11, and a top member or cover 13. Back panel 14 is connected to the respective back ends of the base 11, transverse partition 12 and top 13. A lower front panel 15 is connected to the respective front ends of the base and the transverse partition to define with the back wall, the base and the transverse partition a desorption block compartment 16. Similarly an upper front panel 17 is connected between and inwardly of the respective front ends of the transverse partition 12 and the top member 13 to define with the back panel an upper compartment 18 in which various interrelated controls, gas manifolds, solenoid operated gas valves, etc. hereinafter more fully described are mounted and connected to each other to provide the advantageous and improved operation of the short path thermal desorption apparatus 6 in accordance with the present invention.

FIGS. 2 to 6, 16, 17A, 17B and 17C, further show that housing 10 also includes, a right side wall 19 connected to one side of the base 11, transverse partition 12, and top member 13, and upper left side wall 20a and lower left side wall 20b removably connected to the opposite or other side of the base 11, transverse partition 12 and top member 13. The upper left side wall 20a and lower left side wall 20b are detachably connected as by threaded fasteners for easy removal to provide means for accessing the respective desorption compartment 16 and upper compartment 18 in the housing 10 as may be necessary for maintenance, repair and adjustment of the various operating elements, during the use and operation of the short path thermal desorption apparatus 6.

Lower front panel 15 has an opening 21 which serves both as a view port and a vent to enable relatively cool ambient air to flow from the exterior of housing 10 through the desorption block compartment 16 and out through an outlet vent 22 in the back wall 14 whenever cooling fan 23 is in operation so as to maintain and control the temperature in the desorption block compartment 16 at less then 60° C. for safety purposes and for rapid cooling of the desorption tube or container 7 during the operation of the short path thermal desorption Apparatus 6.

Upper front wall 17 is provided with a vertically extending opening 24 through which a mounting carriage 25 projects and along the length of which vertical opening the mounting carriage 25 will be moved to and from by means of a conventional compressed air powered piston and cylinder assembly generally designated 26, all of which is shown in FIGS. 2 to 6, 16, 17A, 17B and 17C of the drawings.

Compressed air operated power cylinder 26 is an elongated member mounted generally vertically in upper chamber 18 between the transverse partition 12 and the top member 13 just inwardly of the front wall 17 and includes, an elongated hollow air tight cylinder 27 in which a free piston 28 is disposed for slidable movement to and fro along the length thereof responsive to the pressure of compressed gas admitted to the cylinder 27 through gas inlet ports 29 and 30 spaced from each other and communicating with the air cylinder on opposite sides of the free piston 28. Compressed air line 31 is connected at one end to gas inlet port 29 and compressed air line 32 is connected at one end to gas inlet port 30. The respective opposite ends of the compressed air lines 31 and 32 are connected to a solenoid operated compressed air valve 33 which controls the flow of compressed air to the air cylinder 27 to actuate up and down movement of free piston 28.

Thus, solenoid operated compressed air valve 33 will be actuated to charge compressed air into port 29 to move piston 28 down, and at the same time the opposite port 30 will permit air on the opposite or down side of the free piston in the air cylinder 27 to escape. Conversely when the compressed air valve 33 is actuated to charge compressed air into inlet port 30 to move the free piston 28 upwardly, the inlet port 29 will permit air on the opposite or up side of the free piston in the air cylinder 27 to escape.

Compressed air operated power cylinders of the type above described and the associate solenoid operated compressed air valve for controlling the flow of compressed air to the air powered cylinder 27 are well known and are easily purchasable in the commercial marketplace. Therefore, the air operated power cylinder 25 as shown herein will not be more fully described as it will be easily understood by those skilled in the art.

FIGS. 6, 7, 8 and 9 further show that on the outer surface of air cylinder 27, spaced longitudinally extending guide rails 35 and 36 are provided on which the mounting carriage 25 is disposed for sliding movement. Mounting carriage 25 is fixedly connected to the free piston 28 by any suitable means and will slide upwardly and downwardly therewith along the guide rails 35 and 36 when the free piston is actuated for movement by the control valve 33.

The air powered cylinder assembly 26 is positioned in the upper compartment relative the upper front wall 17 so that when the mounting carriage 25 is assembled on the guide rails 35 and 36 and connected for movement with the free piston 28, the mounting carriage 25 will extend through the vertically extending opening 24 in the upper front wall 17 to the exterior of housing 10 where the injector assembly 5 can be fixedly mounted on and moveable therewith on actuation of the free piston 28, all as shown in FIGS. 2 to 6, 16, 17A, 17B and 17C of the drawings.

The mounting carriage will so project beyond the face of the upper front wall 17 that the injection assembly 5 in assembled position thereon will lie and move in a vertical line which passes through the center of access opening 37 in the transverse partition 12 and injection opening 38 in the base 11 disposed in alignment with each other. Thus, when the injection assembly 5 is operated it will be able to coact with the desorption block assembly 9 pivotally mounted in the desorption compartment 16 between the base 11 and the transverse partition 12 for movement from an open to a closed position about the center line or longitudinal line between access opening 37 and the injection opening 38 for reasons that will be clear from the description below of the injector assembly 5 and of the operation of the short path thermal desorption apparatus in accordance with the present invention.

Injection assembly 5 is connected to, supported by and movable with the mounting carriage 25 by means of a gas transfer tube 40 which is mounted in any suitable type of clamping unit as at 41 thereon. Transfer tube 40 has an inlet port 42 at the upper end to which a carrier gas flow line 43 is connected at one end and the opposite end is connected to the solenoid operated carrier gas control valve 43A which acts to control the flow of carrier gas to the inlet port 42 during operation of the short path thermal desorption apparatus 6. A flow controller 43b in line 43 is used to regulate the pressure and rate of flow of the carrier gas delivered to the inlet port 42 for the inlet assembly 5 by means of the manually adjustable knob 43c which extends to the exterior of housing 10, as shown in FIGS. 2, 3, 4, 6 and 16.

The end of the transfer tube 40 remote from the inlet port 42 is threaded as at 44 to enable the threaded inboard end 45 of the desorption tube or container 7 to be detachably connected to the associated threaded end 44 of the transfer tube 40 of the injection assembly 5. The remote end of the desorption tube or container 7 is also threaded as at 46 to enable a corresponding threaded end and locking nut 47 of a needle injector 48 to close and seal the threaded outboard end 46 of the desorption tube or container 7 during the use and operation of the injection assembly 34.

Thus, when the control valve 43a is actuated to charge carrier gas into the injection assembly 5 it will flow into the inlet port 42 and through the transfer tube 40, the desorption tube 7, and then can be discharged with the desorbed sample volatile component through the needle injector 48.

All inner walls of the injection assembly 34 including, the transfer tube 40, the desorption tube or container 7 for storing the sample of the volatile or semi-volatile component and the needle injector 48, which are exposed to the flow of carrier gas are either boro-silicate coated, fused silica lined or lined with materials which are extremely inert, to minimize degradation of the sample of the collected volatile or semi-volatile components being identified and quantified, due to reaction with the inner surfaces of the desorption tube or related portions of the transfer path of the injection assembly 5.

The desorption tube or container 7 is of particular importance to the injection assembly. While it is possible to use glass desorption tubes, such tubes are fragile and for practical purposes may destroy the sample due to breakage. In the present invention, the desorption tube 7 is made from stainless steel tubing having walls with fused silica lining, and detachably connectable stainless steel end covers as at 7a and 7b to send the desorption tube 7 after a simple component is collected and stored therein by being adsorbed onto the trapping agent in the desorption tube 7.

In the collection or storage chamber 50 formed in the desorption tube 7, adsorbent material 51 as a trapping agent is packed such as the porous polymer resin or activated graphitized carbon referred to above. Further the wall 52 of the collection and storage chamber 50, as at 53, will either be coated with a borosilicate or treated to provide a fused silica lining for the purposes and objects as above stated.

These desorption tubes are strong durable traps for both laboratory use and the field collection of samples. Since the lining is extremely inert, reaction or degradation of the sample component in the desorption tube 7 due to contact with the inner wall 52 is minimized.

Figure 17A:
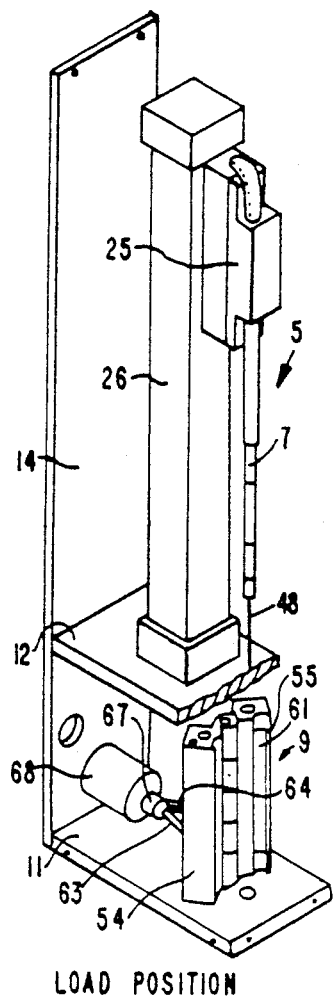
FIG. 17A is an enlarged front perspective diagrammatic view of the actuator, the injection assembly and the desorption block with the injection assembly in the disengaged position for loading the desorption tube in assembled position in the injection assembly.
Figure 17B:
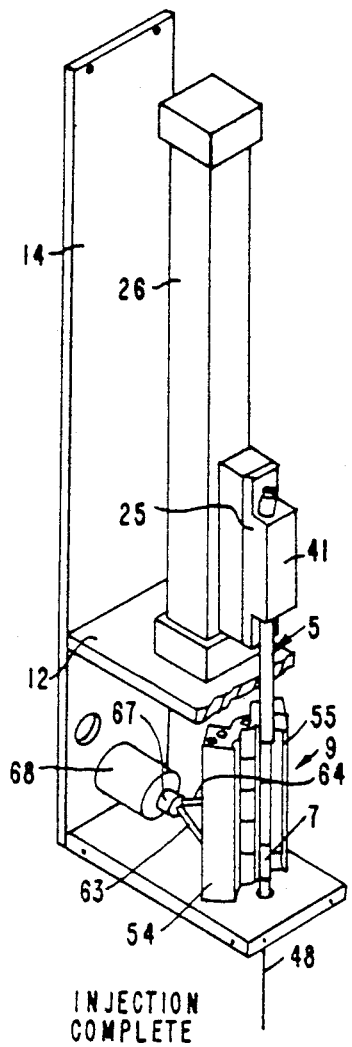
FIG. 17B is a view similar to FIG. 17A with the injection assembly in the engaged position with the desorption tube aligned with the desorption block in the open position.

In order to enable the carrier gas flowing through the injection assembly 5 to properly desorb the volatile component disposed on the adsorbent media 51 in the desorption tube 7, it is necessary to heat and raise the temperature of the desorption tube sufficiently above the boiling point of the volatile component in the desorption tube 7. This is accomplished when the compressed air powered cylinder 26 is actuated to move the free piston 28 so that the mounting carriage 25 will in turn move the injection assembly 5 from its normally disengaged or loading position as shown in FIG. 1A and 17A to the engaged or down position as shown in FIG. 1B, 1C and 17B.

When the injection assembly 5 is so moved the needle injector 48 and the desorption tube 7 will pass through the access opening 37 in transverse plate 12 and injection opening 38 in the base 11 to position the desorption tube 7 in operative alignment with the normally open desorption block assembly 9 and the needle injector 48 in engagement with the inlet port or septum 8 for the capillary gas column 4 of the gas chromatography unit 3. By operative coaction with the desorption block assembly 9 the desorption tube 7 can be heated as may be necessary to raise the temperature thereof to the temperature required to release the sample volatile component in the desorption tube into the carrier gas which is passed through the injection assembly 5 during operation of the short path thermal desorption apparatus in accordance with the present invention.

FIGS. 3, 4, 6, 11 to 16, 17A, 17B and 17C of the drawings show one form of desorption block assembly 9 as having two coacting precision formed elongated heating blocks 54 and 55 which have hinged sections 56 and 57 to enable the heating blocks 54 and 55 to be pivotally connected to each other about the hinge pin 58.

The heating blocks 54 and 55 will be formed and machined from blocks of material which have a high coefficient of heat transfer such as aluminum or stainless steel alloys so the desorption block assembly 9 can be quickly heated and cooled during operation of the short path thermal desorption apparatus 6.

Hinge pin 58 is made of brass and is fixedly connected in the desorption compartment 12 in spaced mounting bushings as at 59 on the lower face of the transverse partition 12 and at 60 on the upper face of the base 11. The bushings are made of a high temperature polyfluorocarbon resin such as "Vespal", and the use of a brass hinge pin in such bushings is to reduce friction during pivotal movement of the heating blocks 54 and 55 and to reduce heat transfer from the heating blocks to the housing. The hinge pin 58 in assembled position is disposed parallel to the vertical line through the centers of the access opening 37 and injection opening 38, and a predetermined spaced distance therefrom so the heating blocks 54 and 55 can be pivoted from their normally open position to a closed or engaged position about the desorption tube 7 when the injection assembly 5 is moved from the disengaged or up position to the engaged or down position as above described.

The heating blocks 54 and 55 are so machined and shaped that mating longitudinally extending grooves 61 and 62 are formed on their respective coacting inner faces and are so sized and shaped that when the heating blocks 54 and 55 are moved from open to closed position the mating grooves 61 and 62 fit snugly about and in engagement with the desorption tube 7, as will be clear from FIGS. 11 to 16, and 17A, 17B, and 17C of the drawings.

In order to actuate and move the pivotally mounted heating blocks 54 and 55 from the open to the closed position and vice versa, spaced lever arms 63 and 64 are connected at one end respectively to a connecting bracket 65 on heating block 54 and connecting bracket 66 on heating block 55 and their respective opposite ends are each connected to the exterior end of plunger 67 of a solenoid operated compressed air valve 68 also fixedly mounted in the desorption compartment 16. The solenoid operated compressed air valve 68 is provided with inlet ports 69 and 70 for charging air into the valve 68 to actuate movement of the plunger 67. The charging air for this purpose is delivered by line 71 connected at one end to inlet port 69 at one end of air valve 68 and line 72 connected to inlet port 70 at the opposite end of air valve 68. The opposite ends of lines 71 and 72 are connected to a source of compressed air through the solenoid operated manifold valve 68A.

When compressed air is delivered to inlet port 69 of component air valve 67 and plunger 67 is moved forward, the lever arms 63 and 64 also move forward, causing the heating blocks 54 and 55 to pivot about the hinge pin 58 to the engaged position about the desorption tube 7 when the injection assembly 5 is in the engaged or down position. Conversely when the compressed air is charged to inlet port 70, the plunger 67 will be moved backwards to move the lever arms 63 and 64 so as to pivot the heating blocks 54 and 55 to the open position. Solenoid operated manifold valve 68A and the compressed air or gas operated valve 68 are well known in the art and easily purchasable in the marketplace, and well understood by those skilled in the art so that the structure and operation thereof except as it relates to the operation of the desorption block assembly 9 will not be more fully described.

FIGS. 11 to 16 and FIG. 19 further show that each of the heating blocks 54 and 55 are provided with conventional resistance heaters 73 and 74 which are longitudinally disposed in each of the heating blocks 54 and 55. Since the heating blocks 54 and 55 form bilateral coacting units, in the closed and engaged position of the desorption block assembly 9 with the desorption tube 7 as above described, the respective resistance heaters 73 and 74 will be in relatively close proximity to the desorption tube 7 to permit accurate ballistic heating of the desorption tube to the desired temperatures for time periods from thirty (30) seconds to one (1) hour. This bilateral coaction between the heating blocks 54 and 55 and there respective resistance heaters 73 and 74 enables the desorption tube 7 to be heated at ramp rates up to at least 100° C. per minute and the attained temperature can be maintained within $+/-5°$ C.

The desorption block assembly 9 also includes a longitudinally disposed platinum resistance thermometer as at 75 which provides feedback to enable the electronic controller 6a to regulate the temperature as well as provide an accurate temperature indication for the coacting heating blocks 54 and 55 for the desorption block assembly 9. The platinum resistance thermometer enables temperature control of the heating blocks 54 and 55 within $+/-5°$ C.

Figure 18:
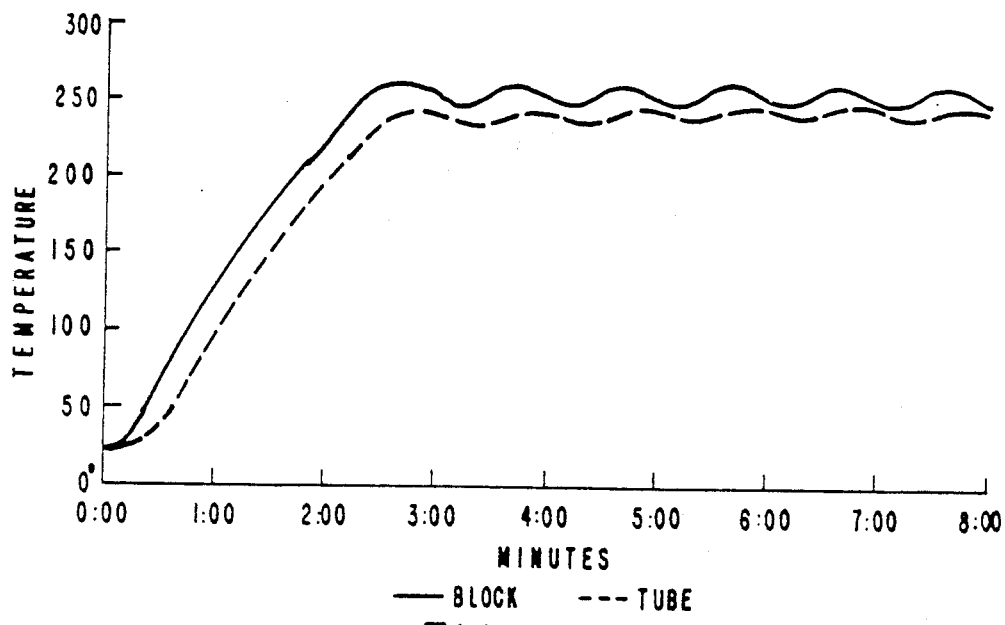
FIG. 18 is a Time/Temperature Graph showing the relative temperatures of the desorption block and the desorption tube over time of operation.
Figure 19:
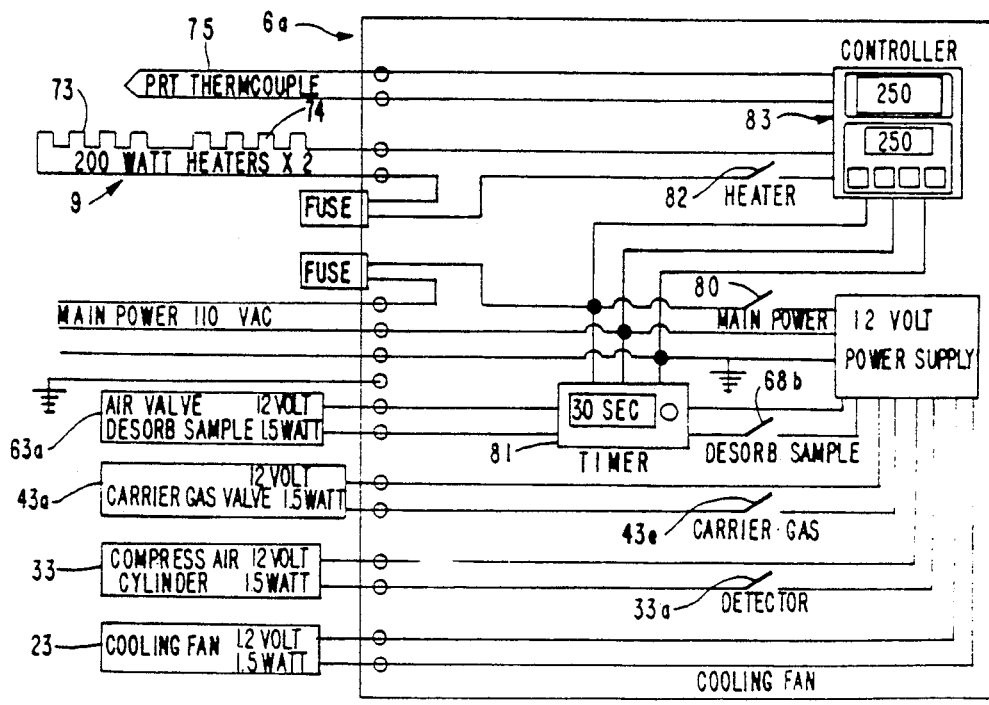
FIG. 19 is a schematic illustration of the electrical circuitry in the electronic controller for operating the short path thermal desorption Apparatus in accordance with the present invention.

FIG. 18 shows a graph of temperature versus time for the respective desorption block assembly 9 and the desorption tube 7 in which the solid line represents the change in temperature against time for the desorption block assembly 9 and the dashed line that for the desorption tube 7. It will be readily apparent from this graph that attained temperature of the desorption tube 7 is within a few degrees of that of the desorption block assembly 9 during the operation and use of the short path thermal desorption apparatus 6 in accordance with the present invention.

It also will be clear from FIGS. 16, 17A, 17B and 17C that in the operative coaction between the injection assembly 5 and the desorption block assembly 9 that the desorption tube 7 will be disposed about 4 cm from the point where the sample volatile component to be measured is injected into the injection port or septum 8 for the gas column 4 of the gas chromatography unit 3. Thus, the sample volatile component will travel a very short distance before it is brought into the GC-MS system for making the identification and quantitative determination of the volatile component.

In the short path thermal desorption apparatus, as above described, reference is made to carrier gas used in the operation of the injection assembly 5 to aid and abet desorption of the sample component from the desorption tube 7. Carrier gas for this purpose preferably will be helium or nitrogen although other types of carrier gas may be utilized under proper safety conditions.

The carrier gas from any suitable source such as a gas pressure cylinder, not shown, is delivered through a carrier gas delivery line 76 to the carrier gas manifold 76A. Carrier gas manifold 76A coacts with solenoid operated carrier gas control valve 43A connected by carrier gas line 43 to the inlet port 42 of the gas transfer tube 40 of the injection assembly 5. A pressure regulator 43B is interposed in the carrier gas line 43 to regulate the pressure and flow of the carrier gas to the injection assembly 5 during the operation of the short path thermal desorption apparatus depending on the required operating conditions for the associated gas chromatography unit into which the sample component will be injected for identification and quantification. A suitable manual control 43C is disposed to extend externally of Housing 10 through the top member 13 so that the pressure regulator can be adjusted by reference to the pressure gauge 43D in accordance with the required operating conditions all of which is shown in FIGS. 2, 3, 4, 5, 6, and 16 of the drawings.

Current for operating the carrier gas valve 43A is delivered from the electronic controller 6A by moving the carrier gas valve switch 43E from the open to the closed position, which will actuate the solenoid to move the carrier gas valve 43A to the open position. Conversely, when the carrier gas switch 43E is moved from the closed to the open position the solenoid will close the carrier gas valve and terminate flow of carrier gas to the inlet port 42 of the transfer tube 40 of the injection assembly 5.

Reference is also made to compressed air for actuating the power cylinder 26 to move the injection assembly 5 from the disengaged to the engaged position and to operate the control valve 68 for actuating the heating blocks 54 and 55 of the desorption block assembly 9. Compressed air is used for these purposes because it is available from many types of suitable sources such as a compressed air tank or an air compressor as at 77. Compressed air is cheap and safe particularly where the air is spilled into the ambient atmosphere surrounding the short path thermal desorption apparatus 6 during the operation thereof.

Compressed air from the compressed air compressor 77 is delivered through compressed air delivery line 78 to the compressed air manifold 78A, which coacts with the solenoid operated compressed air control valves 33 and 68A, for controlling the delivery of compressed air to the power air cylinder 26 for moving the injection assembly 5 from the disengaged position to the engaged position and to the desorption block air valve 68 for actuating the heating blocks 54 and 55 of the desorption block assembly 9.

The solenoid operated pressure air valve 33 is actuated by the injector switch 33A on the electronic controller 6A, which when moved from the open to closed position will actuate air pressure valve 33 to deliver air through line 31 to the inlet port 29 for the power air cylinder 26 and when moved to the open position will deliver air through line 32 to port 30 of the power air cylinder 26, thus, moving the piston 28 therein downwardly and upwardly respectively so that the mounting carriage and the injection assembly 5 connected to the piston, as above described, will be moved therewith to thus move the injection assembly 5 from the disengaged position as shown in FIGS. 1A, 16 and 17A to the engaged position as shown in FIGS. 1B and 17B of the drawings.

Figure 17C:
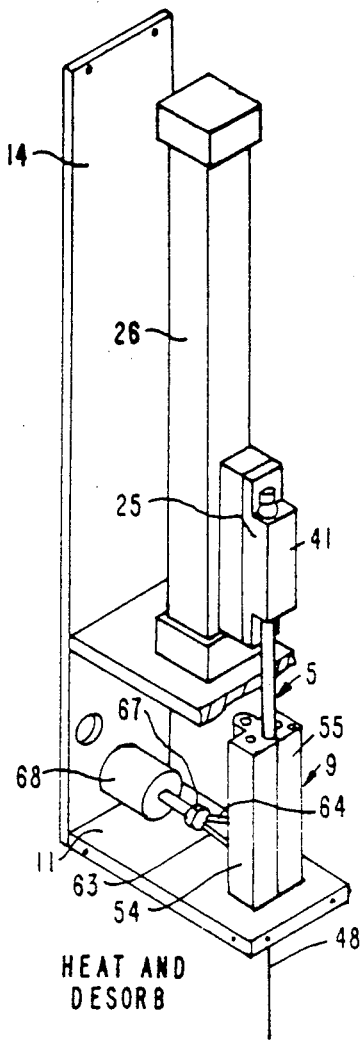
FIG. 17C is a view similar to FIG. 17B with the desorption block closed and ready to heat the desorption tube enclosed therein for desorbing the sample component stored in the desorption tube.

In the case of the desorption block assembly valve 68 the solenoid operator 68A is actuated by the desorption block assembly valve 68B, which when moved from the open to the closed position will deliver air through line 72 to the inlet port 70 for moving the piston 67 to drive the levers 63 and 64 so as to pivot the heating blocks 54 and 55 of the desorption block assembly to the closed position when the injection assembly 5 is in the engaged position, all of which is shown in FIGS. 1B, 16 and 17C of the drawings.

Operation of the solenoid operated carrier gas valve 43A and the solenoid operated air controlled valves 33 and 68A will be controlled by the electronic controller 6A.

Electronic controller 6A also includes a digital timer 81 to control the length of time the desorption block assembly 9 is closed which timer can be accurately and reproducibly set in a range between thirty (30) seconds and sixty (60) minutes to automate the desorbing of a sample component from the desorption tube 7 into the inlet port 8 or the gas column 4 of the gas chromatography unit 3 of the GC-MS system.

OPERATION

Operation of the short path thermal desorption apparatus 6 is designed to provide a wide variety in the modes of operation in that the temperatures and desorbing times can be varied, controlled and accurately repeated as may be necessary by means of the electronic controller 6A, which will be referred in the steps of the method for operating the short path thermal desorption apparatus in accordance with the present invention as will now be described.

1. As a preliminary step to commencing the desorption of the sample component, the main power switch 80 of the electronic controller 6A is turned to the on position and then the heater switch 82 is moved from the open to the closed position to deliver current to the resistance heaters 73 and 74 of the heating blocks 54 and 55. The respective resistance heaters 73 and 74 are set to be maintained at a predetermined temperature by means of the thermal controller 83 and the platinum resistance thermometer 75.

2. While this heating is in progress, the desorption tube 7 has the end covers 7A and 7B removed and it is fixedly threaded into assembled position with the transfer tube 40 and needle injector 48 of the injection assembly 5 at the exterior of the housing 10. Injection assembly 5 is initially and normally disposed in the disengaged or load position for this purpose as is shown in FIGS. 1A and 17A of the drawings.

3. Now the carrier gas is started by pressing the carrier gas switch 43E on the electronic controller 6A from the open to the closed position to actuate the solenoid operated carrier gas valve 43A to deliver carrier gas through line 43 to the gas transfer tube 40, the associated desorption tube 7 and needle injector 48 of the injection assembly 5. Carrier gas is permitted to flow freely through the injection assembly 5 for a sufficient period of time to purge oxygen and moisture from the desorption tube 7. This is done because it will prevent both degradation due to oxidation of the sample component when it is desorbed from the desorption tube 7, and damage to the capillary or packed column 4 of the gas chromatography unit 3.

4. The flow rate of the carrier gas is now adjusted to meet the requirements of the particular gas chromatography unit-detection system being used. Due to the difference in the I.D. and length of the capillary or packed column 4, the back pressure and flow rate of the carrier gas is adjusted preferably prior to movement of the injection assembly 5 into the engaged position. Alternatively, this may be done after the engaged position is reached and the needle injector 48 has engaged the inlet port or septum 8 of the capillary or packed column 4 of the chromatography unit 3.

This is accomplished by means of the carrier gas flow controller 43B and the manual knob 43C for making this required adjustment. A suitable pressure gage 43D is disposed for viewing at the exterior of the housing so that the back pressure and flow rate can be determined accurately.

5. The short path thermal desorption apparatus 6 is now actuated to move the injection assembly 5 from the disengaged or load position, as shown in FIGS. 1A and 17A of the drawings to the engaged or injector position shown in FIGS. 1B and 17B of the drawings by closing the injector switch 33A which delivers current to the solenoid operated compressed air valve 33 moving this valve to the open position to deliver and pass compressed air through line 31 to port 29 to move the piston 28 in the power cylinder 26 downwardly. Since the mounting carriage 25 is connected to piston 28, mounting carriage and the associated injector assembly 5 connected thereto are also moved downwardly until the needle injector 48 engages the inlet port or septum of the capillary or packed column 4 of the gas chromatography unit 3, which action also positions the desorption tube 7 between the normally open heating blocks 54 and 55 of the desorption block assembly 9.

6. While the heating blocks 54 and 55 of the desorption block assembly 9 are at the predetermined temperature as set by the electronic controller 6A by means of the temperature controller 83 and the platinum resistance thermometer 75, the desorption tube 7 although disposed for operative association therewith will, so long as the heating blocks 54 and 55 remain open, stay below the desorption temperature for the sample component because of the cooling effected by the continuous flow of air being pulled through the desorption chamber 12 by the cooling fan 23 all of which is shown by reference to FIGS. 3, 4, 6, 16 and 17B of the drawings.

7. Before desorption is effected and desorption air valve 68 actuated, the electronic controller or data processor 6A is set for the desired temperature and time program for the particular sample component to be desorbed into the carrier gas and injected into the capillary or packed column 4 of the gas chromatography unit 3.

8. Desorption can now be effected by moving the desorption switch 68B from the open to the closed position so that current will flow to the solenoid operator 68A actuating the desorption air valve 68 to actuate the piston 67 and lever 63 and 64 to move the heating blocks 54 and 55 from the normally open position to the closed position about the desorption tube 7, as is shown in FIGS. 1B and 17C of the drawings.

In this position the desorption tube 7 is subjected by ballistic heating to the appropriate predetermined temperature for desorbing the sample component and the desorption tube 7 and after being raised to this required temperature will be maintained at such temperature within $+/-5°$ C. by the platinum resistance thermometer 75 for the required period of time.

9. On completion of the temperature/time program switch 68B is moved to the open position which deactuates the solenoid operator 68A to move the desorption assembly air valve so that the heating blocks 54 and 55 are returned to the normally open position as shown in FIGS. 16 and 17B of the drawing.

Now switches 33A and 43D are opened to move the ejector assembly 5 to the normally disengaged or load position and to terminate delivery of carrier gas to the injection assembly 5.

10. The spent desorption tube 7 and needle injector 48 are now removed from assembled position in the injector assembly 5 and a new desorption tube and needle injector are connected in position to place the apparatus in position to repeat the above steps for the next sample component to be analyzed.

Thus there has been described an improved short path thermal desorption apparatus for universal use with any gas chromatography-detector unit system, method and technique, and more particularly shown herein in use with one such GC-MS system. The improved short path thermal desorption apparatus is portable, easily installed, simple to operate, and provides a short transfer path for the sample component to be measured thus eliminating problems which have affected the prior devices heretofor used for this purpose.

ALTERNATE EMBODIMENT

While the short path thermal desorption apparatus for use in gas chromatography techniques has been described as a device for collecting and storing volatile or semi-volatile components from complex matrices, and adapting the apparatus to release these sample components by thermal desorption, the desorption tube and short path thermal desorption apparatus can also be used for other purposes without departing from the scope of the present invention.

Thus, instead of incorporating a trapping agent in the collecting chamber 50 of the desorption tube 7 the tube can be packed directly with any complex matrix and the carrier gas passed through this complex matrix at any predetermined temperature in the same manner as has been above described for the desorption tube with a trapping agent for collecting and storing a sample volatile or semi-volatile component. As the carrier gas is passed through the complex matrix at the predetermined temperature, the components separated from the complex matrix in such carrier gas can be identified and quantified in the same manner as occurs with the release of the adsorbed sample component as has been above described.

For this alternate form of operation the desorption tube 7 will only require that the inner wall 52 of the chamber 50 be coated with a glass lining or a fused silica lining for the same purposes and objects as stated for the first form of the present invention as above described.

In this form of the invention the desorption tube serves as a heating crucible for direct thermal analysis of any matrix placed in the desorption tube.

Those skilled in the art will recognize that various changes can be made to the form, construction and arrangement of the apparatus as shown without departing from the spirit and scope of the invention, therefore the apparatus as above described is merely illustrative and not limiting except by the appended claims.

What is claimed is:

1. A short path thermal desorption apparatus for use in a gas chromatography-detector (GC-DET) system comprising:
   a. housing means disposed for operative relation with the GC-DET system,
   b. an elongated injection assembly disposed for sliding movement in the housing means from a normally disengaged position to an engaged position with the GC-DET system including, a detachably connectible generally hollow desorption tube means for collecting and storing a sample of a component to be desorbed and delivered to the GC-DET system for identification and quantification, and a needle injection means for injecting the desorbed sample of the component into the GC-DET system,
   c. means connected to a source of carrier gas and to said injection assembly for charging the carrier gas into the desorption tube for desorption of the component sample on heating of the desorption tube, and
   d. heating means pivotally mounted in said housing means including, coacting heating block members disposed for bilateral movement from an open to a closed position and vice versa for engaging and heating the desorption tube when the injection assembly is moved to the engaged position.

2. In the sort path thermal desorption apparatus as claimed in claim 1 wherein,
   a. said housing means has, an upper compartment, and
   b. actuating means mounted in said upper compartment and connected to said injection assembly for moving said injection assembly from the disengaged to the engaged position and vice versa.

3. In the short path thermal desorption apparatus as claimed in claim 1 wherein,
   a. said housing means has, a front panel defining an upper compartment,
   b. said front panel having, a longitudinal opening to provide communication with the upper compartment from the exterior of the housing,
   c. said injection assembly disposed at the exterior of said housing adjacent the front panel, and
   d. actuating means mounted in said upper compartment and connected through the longitudinal opening in the front wall with said injection assembly for moving said injection assembly from the disengaged to the engaged position and vice versa.

4. In the short path thermal desorption apparatus as claimed in claim 1 wherein,
   a. said housing means has, panel means defining a desorption compartment,
   b. the heating means including, a pair of coacting heating blocks disposed and pivotally mounted in the desorption compartment in the housing means, and means operatively connected to the coacting heating blocks to move the coacting heating blocks from open to closed position and vice versa,
   c. said panel means defining the desorption compartment has an access opening in communication with one end of the heating means, and an injection opening in communication with the opposite end of the heating means and spaced from and in alignment with the access opening whereby on movement of the heating means to the closed position the coacting heating blocks will lie in the center line of the access opening and the injection opening, and
   d. said injection assembly disposed for movement from the disengaged to the engaged position also in the center line of the access opening and the injection opening whereby in the engaged position the injection assembly will extend through the access opening and the injection opening so that the desorption tube will be in operative association with the heating blocks and the needle injector will extend through the injection opening for operative engagement with the GC-DE system.

* * * * *

UNITED STATES PATENT AND TRADEMARK OFFICE
CERTIFICATE OF CORRECTION

PATENT NO. : 5,065,614
DATED : November 19, 1991
INVENTOR(S) : Hartman, et al

It is certified that error appears in the above-indentified patent and that said Letters Patent is hereby corrected as shown below:

On the title page:

```
In the Abstract, line 2, "chromatoagraphy-detector" should read
     --chromatography-detector--.
Column 2, line 25, after "Monitoring" insert --,--.
Column 14, line 1, after "1A" change "." to --,--.
Column 17, line 29, "sort" should read --short--.
Column 18, line 40, "GC-DE" should read --GC-DET--.
```

Signed and Sealed this

Eighth Day of June, 1993

Attest:

MICHAEL K. KIRK

Attesting Officer

Acting Commissioner of Patents and Trademarks